US00PP08235P

United States Patent [19]

Warriner

[11] Patent Number: Plant 8,235

[45] Date of Patent: May 25, 1993

[54] ROSE PLANT JACSOS

[75] Inventor: William A. Warriner, Tustin, Calif.

[73] Assignee: Bear Creek Gardens, Inc., Medford, Oreg.

[21] Appl. No.: 625,871

[22] Filed: Dec. 10, 1990

[51] Int. Cl.[5] ..... A01H 5/00

[52] U.S. Cl. ..... Plt./1

[58] Field of Search ..... Plt. 1, 28

*Primary Examiner*—Howard J. Locker

*Attorney, Agent, or Firm*—Klarquist, Sparkman, Campbell, Leigh and Whinston

[57] ABSTRACT

A rose plant from the shrub class having upright free-flowering habit of growth, continuous flowering, dark green, semi-glossy foliage, ease of rooting as a softwood or hardwood cutting and profusion of glands on sepals, receptacle, and rachis.

1 Drawing Sheet

1

The present invention relates to a new and distinct variety of rose plant of the shrub class which was originated by me by crossing the variety Tanweieke, U.S. Plant Pat. No. 4,844, with the variety Jacink U.S. Plant Pat. No. 4,089.

The primary objective of this breeding was to produce a new rose variety having the upright free flowering habit of growth of variety of Jacink of with the dark, glossy green foliage and orange-red flower color of Tanweieke. The objective was substantially achieved along with other desirable improvements as evidenced by the following unique combination of characteristics which are outstanding in the new variety and which distinguish it from its parents, as well as from all other varieties of which I am aware:

1. Upright free-flowering habit of growth.
2. Continuous flowering.
3. Dark green, semi-glossy foliage.
4. Ease of rooting as a softwood or hardwood cutting.
5. Profusion of glands on sepals, receptacle and rachis.

Asexual reproduction of this new variety by budding and by softwood and hardwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—Tanweieke, U.S. Plant Pat. No. 4,884.

*Pollen parent.*—Jacink U.S. Plant Pat. No. 4,089.

Classification:

*Botanical.*—Rosa hybrida.

*Commercial.*—Shrub.

2

FLOWER

Observations made from specimens grown in a garden in Somis, Calif., in September, 1990.

Blooming Habit: Continuous.

Bud:

*Size.*—1 to 1½ inches when the petals start to unfurl.

*Form.*—Short, pointed ovoid.

*Color.*—When sepals first divide, bud color is Red Group 45C. When half blown, the upper sides of the petals are Red Group 45D; and the lower sides of the petals are Red Group 45D.

*Sepals.*—Color: Green Group 139C. Surface texture: Covered with fine hairs. There are three normally to heavily appendaged sepals. There are two unappendaged sepals with hairy edges and numerous glands.

*Receptacle.*—Color: Green Group 143B. Shape: Funnel. Size: Small (⅛×3/16″). Surface: Glandular.

*Peduncle.*—Length: Short (1½to 2″). Surface: Glandular. Color: Bronzy. Strength: Stiff, erect, slender.

Bloom:

*Size.*—Medium. Average open size is 3 inches.

*Borne.*—Singly and several together in pyramidal clusters.

*Stems.*—Medium (14 to 16″), strong.

*Form.*—When first open: Cupped, becoming flat very quickly. Permanence: Flattens.

*Petalage.*—Number of petals under normal condition: 15 to 20.

*Color.*—The upper side of the petals is Red Group 45D. The reverse side of the petals is Red Group 45D. The base of each petal has a very small greenish white half moon white group 155a, at the point of attachment (1/16″×1/16″). The major color on the upper side is Red Group 45D.

*Variegations.*—None.

*Discoloration.*—No change in the general tonality at the end of the first day. No change at the end of the third day.

*Fragrance.*—Slight.

Petals:

*Texture.*—Thick, leathery.

*Shape.*—Deltoid.

*Form.*—Tips slightly recurved.

*Arrangement.*—Imbricated, with few petaloids in the center.

*Persistence.*—Drop off cleanly.

*Lastingness.*—On the plant: Fair (3 to 4 days. As a cut flower: Long (5 to 7 days.

Reproductive parts:

*Anthers.*—Size: Medium. Quantity: Many. Color: Yellow. Arrangement: Regular around styles.

*Filaments.*—Color: Yellow with some reddish blush.

*Pollen.*—Color: Lemon yellow.

*Styles.*—Color: Reddish yellow.

*Stigmas.*—Color: Greenish white.

Form: Shrub.

Growth: Very vigorous, upright, branching.

Foliage: Number of leaflets on nornal mid-stem leaves: 5.

*Size.*—Medium (4½"×3").

*Quantity.*—Abundant.

*Color.*—New foliage: Red. Old foliage: Dark green and semi-glossy.

Leaflets:

*Shape.*—Pointed oval.

*Texture.*—Upper side: Semi-glossy, smooth.

*Edge.*—Serrated.

*Serration.*—Single.

*Petiole rachis.*—Color: Reddish when immature, becoming green.

*Petiole underside.*—Smooth with a few glands and an occasional small prickle.

*Stipules.*—Medium (½"), bearded.

*Disease resistance.*—Susceptible to mildew; resistant to rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium to short (¼"), hooked downward.

*Color when young.*—Red.

Small prickles:

*Quantity.*—On main stalks: Few. On laterals: Few.

I claim:

1. A new and distinct variety of rose plant of the shrub class, substantially as herein shown and described, characterized particularly as to novelty by the unique combination of its vigorous upright habit of growth, its continuous production during the growing season of light red flowers, its dark green, semi-glossy foliage, its ease of production from softwood or hardwood cuttings and its profusion of glands on sepals, receptacle, and rachis.

* * * * *

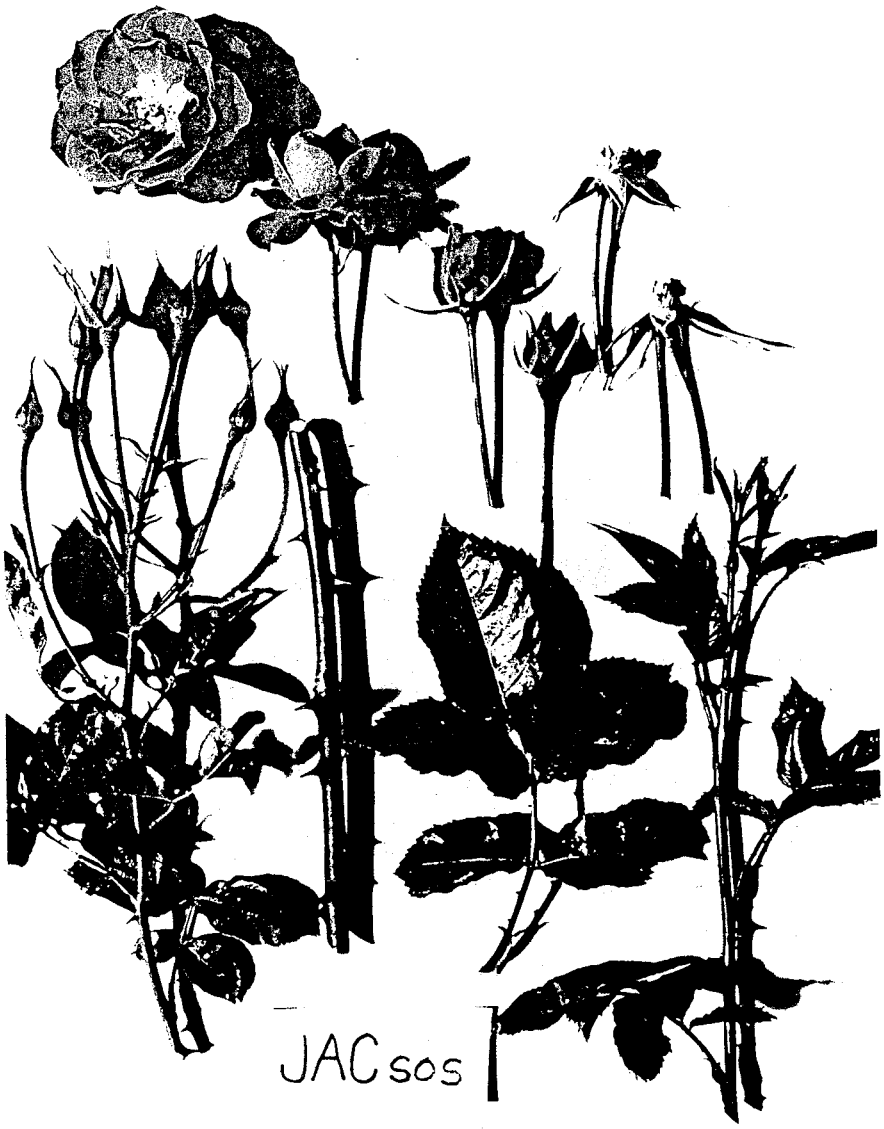
JAC sos